United States Patent
Mollet et al.

(10) Patent No.: US 6,331,140 B1
(45) Date of Patent: Dec. 18, 2001

(54) **MOBILE GENETIC ELEMENTS AS TOOLS FOR GENETIC MODIFICATION OF *L. DELBRUECKII* OR *L. HELVETICUS***

(75) Inventors: Beat Mollet, Lausanne; Jacques Edouard Germond, Crissier; Luciane Lapierre, Attalens, all of (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/334,938

(22) Filed: Jun. 17, 1999

(30) Foreign Application Priority Data

Jun. 17, 1998 (EP) .................................................. 98202028

(51) Int. Cl.$^7$ .......................... C12N 15/74; C12N 15/00; C12N 1/20; C12Q 1/02
(52) U.S. Cl. ................... 453/476; 435/320.1; 435/252.3; 435/29
(58) Field of Search .............................. 435/440, 252.31, 435/7.32, 476; 536/23.1

(56) References Cited

FOREIGN PATENT DOCUMENTS

0441991A1 * 2/1990 (EP) ................................ C12Q/1/68
0 603 416 A1 6/1994 (EP) ..................................... 435/440

OTHER PUBLICATIONS

Molecular and General Genetics, vol. 248, No. 4, Aug. 1995, pp. 407–416, "A new mobile genetic element in *Lactobacillus delbrueckii* subsp. *bulgaricus*", Germond et al.

Gene, (Jul. 22, L994) 145 (1) 75–9, "Characterization of IS1201, an insertion sequence isolated from *Lactobacillus helveticus*", Patrick Tailliez et al.

Antonie Van Leeuwenhoek, Oct. 1996, 70 (2–4) 161–83, "Genomic organization of lactic acid bacteria", B. Davidson et al.

Molecular and General Genetics, vol. 245, 1994, pp. 334–338, "ISL2, a new mobile genetic element in *Lactobacillus helveticus*", Zwahlen et al.

Iida et al. "Mobile Genetic Elements", p. 192, Academic Press, Inc. New York, Shapiro, ed. (1983).*

Stingele et al. "Identification and characterization of the eps (Exopolysaccharide) gene cluster from Streptococcus thermophilus Sfi6", J Bacter 178:1680–1690 (1996).*

Horodniceanu et al. "R plasmids in Streptococcus agalactiae (group B)", Antimicrob. Agents Chemother. 10:795–801 (1976).*

* cited by examiner

*Primary Examiner*—Ponnathapu Achutamurthy
*Assistant Examiner*—David J. Steadman
(74) *Attorney, Agent, or Firm*—Winston & Strawn

(57) ABSTRACT

The use of a IS-element as a tools for genetically modifying the genome of *Lactobacillus delbrueckii* or *Lactobacillus helveticus*. An IS-element, originating from *Lactobacillus delbrueckii* selected from the DNA sequences SEQ ID NO: 7–10 or functional derivatives thereof. A *Lactobacillus delbrueckii* or *Lactobacillus helveticus* providing a gene encoding, or affecting the production of, enzymes producing secondary metabolites, the β-galactosidase, the cell wall protease, the catabolite control protein A, the lactate dehydrogenase, a glycosyltransferase, a restriction system, a lysogenic prophage, or the permease of the lac operon, wherein the gene is inactivated by insertion of at least one IS-element. The use of the above-mentioned *Lactobacillus delbrueckii* or *Lactobacillus helveticus* for the preparation of a fermented product.

8 Claims, No Drawings

SEQUENCE LISTING

<160> NUMBER OF SEQ ID NOS: 22

<210> SEQ ID NO 1
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 1
cctggttgac ttccgcttc                    19

<210> SEQ ID NO 2

-continued

```
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 2
gtaagttgtt tgagagc                                                        17

<210> SEQ ID NO 3
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 3
cctttggtga caatgtc                                                        17

<210> SEQ ID NO 4
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 4
ggttaatgcc gccaaagt                                                       18

<210> SEQ ID NO 5
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 5
ctggaaacac attactg                                                        17

<210> SEQ ID NO 6
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 6
agaaatcgtt ccaaccg                                                        17

<210> SEQ ID NO 7
<211> LENGTH: 1658
<212> TYPE: DNA
<213> ORGANISM: L. Debrueckii  Sbp. Lactis

<400> SEQUENCE: 7
acatactaac ctagtgttgg atgattactc gacggagtag tcgttcaaca cttttcttt          60 tactatgtaa agtggagatg aagccaatgc cgtgagctct ttggacacac gatgtcgtaa        120
ataaaacggg cagcttcacc attcaattga gaatctcgtc taagtatgtt gactgttaaa       180
gtcctgttga gaaaattaga tctaattgaa ttgggtgaag gcagctcatc tccgagtaaa       240
gcggaggttt attcttatgg atttattgaa aactgttttc ggtattgatg ttagcagccg       300
gaagtctaac gtatgcatta tggtcaatgg caaaaaagtt aatgactatg ccatctccaa       360
cgatatggta ggcttcaatc ggctgatagg tgaccttaag caggttacta aaccgcagat       420
```

-continued

```
tatctttgaa gcaactggcg tctattccag aagactccag gcgttcttgg acatgcacga      480
attgcgctat gtcatgacga atccgctaga agccaaaaga aagacaaagg atgacctgca      540
ccagaacaag accgataagc ttgatgcctt gcatcttgcc aagctgcagt ctgagcaccc      600
gcaacggctg gcctacgttc aaaacaaaga atatcaagaa ttgatggcca ataaccgcat      660
ctatgaacag gcttcgcacg atctgataac caacaagaat agactgcaca aagcagttca      720
gctcactttc ccagagattg aacacttact ggctaatccg agagggaaaa actactggag      780
tattgctctc agattcccac atccagatat cgtactagaa acaaaagaag ccgatatcat      840
cgacttctta aaaggcttat ctggtattgg taaaaagcgc gctaatgaca taacgcaaaa      900
ccttattcgt ttggctaaag tcgcatgccc agcggtcaaa agaacagtg ctcatattcg       960 tggcctcaaa atggctatta caacattct gagcgctgaa gaagagtgcc agactgcttt      1020
acaggagatg gcaaagctgg ctcctaaacg ggatctggga tcctcacaa gcattccagg      1080 catcggcgaa aacactgctc taagaatcat tagtgagctt ggggatatca gacgttttaa      1140
caaccctagc caattaaatg ccttcgttgg tgttgatcct caagtttatg aatctggcaa      1200
tctcacggcc cacctgtcaa tttcaaagcg tgggacggct attggcagaa aggtgctgta      1260
cttggccata aaccaaattc agtcggctaa gaaagtggga aacccttgtc atattgcgga      1320
ttattacgag aaacgaaaac ggccttctga gactgcaagt cacaagaagg ccgctatcgc      1380
atcgatccat aaattattac ggacgatctt cgctttaatt aagaatgatc aattgtatag      1440
ctatgacgta gccaaacata accaaagact tttgtcataa aaattgatcc aatagatatt      1500
ataacagcct ctttttttgaa attacagaag gtggctgtat ttaccatgcc ctaaatcaga      1560
tatttgtctt gattctccgg gagctatttc ccgattaggc ccttatttca aaataaaatt      1620
gcctaaaatc gttgataaca cttgacttag agtagaaa                              1658
```

<210> SEQ ID NO 8
<211> LENGTH: 1590
<212> TYPE: DNA
<213> ORGANISM: L. Helveticus

<400> SEQUENCE: 8

```
cttaaacttc ccacttacaa aagtgggctt gtaccttgaa aattcaatag tttagccaat      60
aaaaaagcac aaggcctttg ttcgcttgat ataattaagt cgatcaaaac atcatcaata      120
tcaaacgaaa ggttgcgcta tgtctagttt accatcattc gatactgaaa acgaacctaa      180
aattgcccgt tctgttgaaa agttcttcaa ggactacaaa gttatggagc ttctccgtag      240
atgtgggctc cgcaagtcca aaggaatccc actttggtcg atccttttcat acatcttcag      300 taatgtgttt cgagacagaa gcatgtacat gcaacagaag tatggcaagt gtactgctgg      360
cttctccaaa aacacctact atcgattcat gcagaaccca catatcaact ggcttcgcct      420
cactattctg ctagctgaga ggatcgtcaa tgggcacctg aaagatctga cttctgacca      480
acgtgccgat tgcttcgtct ttgacgattc gctctactct agaactggat acaagaagac      540
tgagctggct gccaaagtat tcgaccacgt ttcgatgacc tacaagaagg ctttcgaat      600 gatgaccatg ggttggactg atggatcctc ctttgtccca atcgcttcat cactcttgtc      660
ctcaaagaac gatcagaatg accaagaaga tcgacaagcg cacaatcgcg ccaagaggc     720 ggattatggc ccaatcaaag gggaccgatg tagttatcca gctgctcgat caagccttga      780
aagcagggct cactgccaag tacgtcatgt ttgacacttg gttctccaat cctcatcaga      840
```

-continued

| | |
|---|---|
| ttgtccaaat cagtcaacgt ggtttgaacg taatcgccat ggtgaagaaa agctccaaga | 900 |
| tcacatacga gttcgaagaa aagcggatga acgtcaagca gatcttcaac gcatgcaaga | 960 |
| aacgtcgagg tcgttcaaga tatctcctgt ccgtccctgt aaaggttgga gatcctgcca | 1020 |
| agatggtgc ccagattgat gccagaatag tctgcgtaag aaatcgttcc aaccgcaaag | 1080 |
| actggatcgc tcttatttgc acggacatga cgatcgatga aaatgagatc atcagaattt | 1140 |
| acggcaaaag atgggacatc gaggtcttct tcaagacctg caagagtttc ttgaagcttg | 1200 |
| gcactgaata ccatggcctg tcatatgatg cattgactgc ccatacagct ttcgtctttc | 1260 |
| tgcgctacat gttcatgtca gttgagaagc gagatgatga agatgatagg acaataggcg | 1320 |
| agctctttta ttgcatggta gacgagcttg cggacatcac tttctattac tccctacaaa | 1380 |
| ccctggtgga agccatgttc gagagtgtga aagagatctt ccaaccgaca aagagcaga | 1440 |
| tggaaaggtt caccaacgct ttcatttcac gcctcccgaa gtacatgcaa gaggctatat | 1500 |
| cgccatcatt agcagcttaa ttgaatattt actggctaaa ctattgagtt ttcaaggctt | 1560 |
| catagttctt tttggtgtgg gaagtttaag | 1590 |

<210> SEQ ID NO 9
<211> LENGTH: 1458
<212> TYPE: DNA
<213> ORGANISM: L. Debrueckii

<400> SEQUENCE: 9

| | |
|---|---|
| gatatgaccc ccgaaattag gacactaatt tcggggttta ttttcatgac taaatacact | 60 |
| aaagaaatca aacttgctat ctaccacgaa tgggtagacg accacagaag aggcacctac | 120 |
| cttagccaaa aatatgggat ggggcgtgga ggtatccatt atttggtaga cttgatccaa | 180 |
| aagcatggtg aagatattct ggatcgacct caacagaaat atactgctaa tttcaagctt | 240 |
| gctgccattg atagagttct gctaggcggt gaagcactta gccaggtttc tctagactta | 300 |
| gggcttacaa atacaggaat tcttgcaaat tggcttcgct cttttaaaga aagcgggtat | 360 |
| actgtcatta ccaagaagaa aggtagacca cccaagaatg cccaaaagca aggacaaaca | 420 |
| acggatcaaa gagctggaag agcaggtaaa gaggcttaca gtcgagcttg catacataaa | 480 |
| aaaattggag gccttaattc aagaacggaa gagccaagaa aagaagaatt agctcgtgca | 540 |
| atcactgaat taaggcaaga attgcggctt agcgttaagt acattatcga cgttatcaat | 600 |
| gccaaccctg gattgcctca tatctcaaga agtaactact actaccaaac ccataagcct | 660 |
| gataaggatt ctggtaacca gaagctgatg gatagaatca agagatctt tcttgaacac | 720 |
| agccgacgct atgggtaccg gcgaatctac ggacagcttc gccgggaagt ctatgagatc | 780 |
| aaccataaga aggtgcagag gctcatgcaa aagatgggct tattcgccat ctcaatccgc | 840 |
| aagaaacgca aatacagcag ctattacggc gttcaaggca agatcaagcc agacttaatc | 900 |
| aagcgcaatt tttacgcaat tattcctgac agacattggt ttactgacgt gactgaattc | 960 |
| catcttaaag atcaaaagtt ctaccttttct ccaattatcg atggttgtac ccaagaaatc | 1020 |
| atctcctaca acatttctag gcacccagac cttaagcaag tgatgaccat gctagatgac | 1080 |
| gcatttgaga agcacccggc tcttaacggg cttattttcc actcagaccg tggctggcaa | 1140 |
| tatcagcacc aagcatatca agccgctctg gctaacagag ggatcgatca agtatgtcc | 1200 |
| aggttgggta attctcttga tgacggctta atggagggct tcttcggcat tcttaagcgg | 1260 |
| gagatgttct acgccaaga acataaatac aaggacctaa atgagcttga gcaagctatt | 1320 |
| cacaaataca tcgattacta caacaacgta agaatcaaga caggacgaaa aaacatgacc | 1380 |

```
ccgattgaat atcggaatca tgttttaaca accttaacgg cgtaatacta aattgtccca    1440
attttggggg tcacatca                                                  1458

<210> SEQ ID NO 10
<211> LENGTH: 1239
<212> TYPE: DNA
<213> ORGANISM: L. Debrueckii  Sbp. Bulgaricus

<400> SEQUENCE: 10
cgccgattgt aaaattaaac tgaacactgt tccgatccag taagaaaaat cgttttcact      60
ggattagagc acaaaaaatc catttcaacc atctggtaga atatgaatta ccacaaacat     120
ttctagagag gttaaaatgg atcattcata ttctaacact aaaccacacc aaaagggcaa     180
gcaccttacg ctaaacgacc ggactacaat ccaggagctg cactctaagg gctactctaa     240
tcgtgctata gctagagaac ttaactgctc accaagtacg gtcggatatg agctcaaaag     300
aggcacagta tccctgtata ccggcaatgt gaagcggtat aaagctgtcg aagggcaaag     360
cacttacgaa ctacatagaa gcgaatgcgg ccgcaagagc ttgtttcttc gcagacaaaa     420
gttcatcgac tatgtttccc actgcttcca taatcgaggc tggtctcttg atgcttgcgt     480
gggttatgct ttggccaagg gaatcttcca gaaggatcag gtcgtatcaa ccaaaactct     540
gtataactac gttgacttgg gcctaatgga tatcaagaac ggtgatcttc cagagaaggt     600
caagcgcaat actaagactc gtcgtgtccg tgtaaacaag cgtatcctgg gacgaagcat     660
cgatgaacgt agtcctagaa tcgaaagccg taaggacttt ggccactggg aatgcgatct     720
ggttcttgga cacaagacta aggacgacga tgtgttgctt actctgtgcg aacgaaagac     780
gcgtcagttc ttcatgatca agattgagga taagacctca gctagcgtta tgaaggcatt     840
tgataagctt cgagagtact acggatccaa atggaatcaa atctttaagt ctatcacaac     900
tgacaacgga tctgagttcg cagatctatc caatcttgag caagtttcca agactcttgt     960
gtactacgct catccttata catcctgtga taaaggcagc gtagaacggc acaacggtct    1020
tatcagacgc tatattccca agggagaccg tatggataag tacagtgtgg aagatattgc    1080
taagatcgag gtatggtgca actctcttcc tcggaagatc ttaaactaca agactccaga    1140
agagtacttt gacaccgaac ttgaccgcat ttaccggcgt agatagtcaa aatctgccag    1200
atgttatggt aagtgttcaa tttattcttg caattggcg                           1239

<210> SEQ ID NO 11
<211> LENGTH: 1494
<212> TYPE: DNA
<213> ORGANISM: L. Helveticus

<400> SEQUENCE: 11
ggctctataa tttttttttac tgatggatgt caagtaatac atccgtcggt aagatttttt     60
gcttaaaata aaaagaggc ccataggcct cgctattcgt aacttaaaat cctctaccac     120
aattcttcta agtatagaaa gctggtttct atgaaccta ctgctaatta tattgaaaac      180
ttgcttaatg ttaaagaccc ttgcctaaat tttgtagatt gctctcaaac aacttacaag     240
gggagaaaag taatcatgtg tacagccatt gccgagctcg acacatgtcc taattgtaaa     300
tctgctgatt actatatata taacggcttc aaggtcgttc atatccctta tatttcagct     360
gacgaaagca atccagtcat tatcaaagtc aagaagcacg gtatttttg taagaactgt     420 gagctataca gttatccgtc tacccaaatc gttgacaagt attgccacat ctctaacgcc     480
```

```
gttaaacgta agatcattgt cggactcact aaagatcatt ctatgaccag tattgctgaa      540
gagaatggtg tatcagttac tactgtgcaa agatacttag acaactgcag cgctcaattt      600
actccttcat tcgattcttt gccagaacac ttagcgtttg atgaatttag aggtgtgggg      660
cgaaagctac actttatctg tcaagatggc gaaaaacata ccatcgtcgc cattttagag      720
aatcgcttca aaaacactat tattaaatac tttttgcagt tcccggaaat agttagaaag      780
actgttagaa cagtaagtat ggacctcaac tgctactacg gtgatattgt gcgtcagatt      840
ttcccaaacg ccgagcttgt cattgaccgt ttccatatgg ttcaaatggt aaacagatcc      900
tttatcggtt ttagagttca agtcatgaaa cagttagata agaaatccag agaatacaag      960
cttctaaaac gatattggaa gctgtatatg aagaaatata aggatctgga aggcagtaaa     1020
caattttatg acagatgtct taaagtaccg tatacaccgg ctcaaatcgt tgatgaaggc     1080
cttaaatgca atgaaacact gaagaacaca tacgacttca tgcaggattt cgtgtatgct     1140
ttagcagaca aagatacgaa aaaaattaac gatctgctcg acagtaatat cggtcagtat     1200
tgtgagcgat tgaaaacaac catacggacc cttagaaaga acaggagggc tgtcattaat     1260
ggtgccaaaa tgtcgtactc aaatggctgc ctagagggcg ttaatcgtaa gatcaaacaa     1320
attgaacgta cagcctatgg ctattctaat ttcactcacc ttttgaaaag gatcagacta     1380
gagcagaaca tcatttgctt caaaaaagca ctaaacagac gtgttctgtt tagtgccttc     1440
atcaaacata tgtaagattt cttgacaagc atcagtaaga tttgacaaag agcc           1494
```

<210> SEQ ID NO 12
<211> LENGTH: 858
<212> TYPE: DNA
<213> ORGANISM: L. Debrueckii Sbp. Bulgaricus

<400> SEQUENCE: 12

```
agagttactg cgaaacatct gctataatct taaattatga aatacgaaac agctaaaaat       60
ttaaacaata ccagattcaa gcgtctgatc ggcgttgcca agcctgtctt tgacgaaatg      120
gtcaaagtat taaagccga atatcaagtc aagcatgccc gaggcggcag aaagcccaag      180
ctggcaattg aagacctgct tctggctact ttgcagtacc tcaaggaata ccgtacttat      240
gaacaaatag ctgccgatta cggtgtgcat gacagcaacc tgatcagaag aagccactgg      300
gccgaagaga ctttggttaa gcatggcttt aacattggca agcaagaaat caagccagac      360
gatgttgtct taatcgatgc cactgaagta aagattcaac gcccaaaaaa agacaagcag      420
cttattattc cggcaagaaa aagcagcacc gttttaaaag cccaggcgat tacagacact      480
accggcagaa ttattcattt agacagctgc caggcatacc ggcatgacat gcggctgctg      540
cgtgagtcaa ggcgcagtct gcaccgatcc ggtttgattt tagcggatag cggctatcag      600
ggattggaca agatttactt tcaggcaaaa acaccggtca aatccagcaa gaagaaaccg      660
ctgactcagc aggacagaga gctgaatcat ttaatttctt caattcgaat caaggtcgag      720
catgtatttg gcaaggtcaa agcatacaaa atatttccta ctacgtatcg caatcatcgc      780
cgacgtttta atttaagaat gaatttaatc tgcgggatca tcaaccaaga actggctatc      840
tagtttcgca gtaactct                                                    858
```

<210> SEQ ID NO 13
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 13
ataatagtcg acaatttagg cagac                                    25

<210> SEQ ID NO 14
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 14
aatactgcag gtctgatgtg acc                                      23

<210> SEQ ID NO 15
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 15
ataatagtcg actcacatca gactc                                    25

<210> SEQ ID NO 16
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 16
aatactgcag aacttgttta cgc                                      23

<210> SEQ ID NO 17
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 17
agctttctgg gacaagg                                             17

<210> SEQ ID NO 18
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 18 cttttttgagc atccaggc                                           18

<210> SEQ ID NO 19
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 19
ttcgatccca gttccaag                                            18

<210> SEQ ID NO 20

-continued

```
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 20
cctgcaatta ctaacacg                                                 18

<210> SEQ ID NO 21
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 21
ataatactgc acatcaaaga gaacg                                         25

<210> SEQ ID NO 22
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 22
aatactgcag ccaaagatgc acg                                           23
```

US 6,331,140 B1

MOBILE GENETIC ELEMENTS AS TOOLS FOR GENETIC MODIFICATION OF L. DELBRUECKII OR L. HELVETICUS

STATE OF THE ART

Bacterial insertion sequences (IS) were discovered during early investigations of gene expression in *Escherichia coli* and the bacteriophage lambda. They range from 800 to 2'500 bp in length and can be found in the genome of many different bacteria at numbers varying between a few and a few hundred copies per genome. Most of the insertions sequences contain one large open reading frame (ORF) which extends almost the entire length of the element and encodes for the transposase. IS-element are characterised by the presence at their termini of inverted repeats (IR) which are functional sequences required for transposition. One characteristic of the majority of known insertion elements is that they generate direct repeated duplications (DR) of the target DNA at the point of insertion. The number of base pairs duplicated is specific for each element.

IS-elements have been discovered to play an important role in producing spontaneous mutation in bacteria. Early estimates of the frequency of insertion mutations were made for the galK (Jordan et al., Mol. Gen. Genet., 102, 353–363, 1968) and the lac region (Malamy, In: The lactose operon, Ed. J. R. Beckwith and D. Zipser. Cold Spring Harbor Laboratory, N.Y., 1970). In each case, it was estimated that between 5 and 15% of spontaneous mutations were due to IS insertions. The capacity of certain insertion sequences to generate deletions of neighbouring DNA was first noted for an ISI located in the gal open (Reif et al., Mol. Gen. Genet., 137, 17–28, 1975). IS-elements also contribute to DNA rearrangements by providing homologous DNA for general recombination systems, leading to gene duplication and more complex DNA restructuring.

IS-elements usually contain transitional and transcriptional start and stop signals. Depending on their location, they may interfere with the regulation of adjacent genes. This regulatory potential, together with the DNA rearrangements associated with IS-elements, may help to expand a selective advantage to the population of organisms harbouring mobile genetic elements. Furthermore, the IS-mediated association of functional genes with transmissible episomes facilitates the horizontal spreading of bacterial gene.

IS-elements are further characterised as useful genetic tools. Thus, they are able to translocate from an appropriate vector, i.e. a conjugated or transformed plasmid, onto the bacterial genome and to select their site of integration in a quasi random way. This characteristic can be used in combination with an appropriate selection system to genetically identify (tag) genes or gen-clusters responsible for a specific functionality. This has been demonstrated for the identification of genes responsible for the production of exocellular polysaccharides in *Streptococcus thermophilus* (F. Stingele et al., J. Bact, 178, 1680–1690, 1995. Integration of an IS-element into a functional gene can thereby completely inactive its function.

Furthermore, IS-elements located on extra chromosomal plasmids can integrate in a replicative manner into a bacterial genome, by integrating as a consequence at the same time the entire (or at least a part) of the host plasmid vector into the genome as well. Thereby, the active IS-element duplicates itself and now flanks the integrated plasmid on both sides (Iida et al., In Mobile genetic elements, Shapiro (ed), Acad. P., New York, pp 159–221, 1983). With this method, genes of interest carried on plasmids can be functionally integrated into bacterial genomes.

Three IS-elements originating from lactobacillus have been only characterised. These elements are known to be very specific to a species, which means they are not always active in another species. Shimizu-Kadota et al. identified an IS-element from Lactobacillus casei (Mol. Gen. Genet., 200, 193–198, 1995). Zwahlen et al. also identified an IS-element from *Lactobacillus helveticus* (Mol. Gen. Genet, 245, 334–338, 1994), whereas Germond et al. identified another IS-element from *Lactobacillus delbrueckii* sp. *bulgaricus* (Mol. Gen. Genet., 248, 407–416, 1995).

These lactobacilli IS-elements were never used, or intended to be used as tools to modifying genetically the species from which they come from. One of the reason is because lactobacilli used for yoghurt production are known as being notoriously difficult for genetic modification. In particular, genetic tools for *Lactobacillus delbrueckii* and *Lactobacillus helveticus*, two microorganisms that are phenotypically closely related (see EP441991 and EP391039), are very limited or quasi absent as for today.

The objective of the invention is to provide new genetic tools specifically for the *L. delbrueckii* and *L. helveticus* species, which can be used in genetic gene identification (tagging), gene inactivation, gene integration, and/or gene expression on a plasmid and/or genomic level.

SUMMARY OF THE INVENTION

Accordingly, the present invention thus relates to the use of an IS-element as a tool to genetically modify the genome of *L. delbrueckii* or *L. helveticus*.

In another embodiment, the present invention also relates to an IS-element, originating from *L. delbrueckii*, selected from the DNA sequences SEQ ID NO:7–10 or functional derivatives thereof.

In another embodiment, the present invention also relates to any *Lactobacillus delbrueckii* or any *Lactobacillus helveticus* providing a gene encoding, or affecting the production of, enzymes producing secondary metabolites, the β-galactosidase, the cell wall protease, the catabolite control protein A, the lactate dehydrogenase, a glycosyltransferase, a restriction system, a lysogenic prophage, or the permease of the lac operon, wherein said gene is inactivated by insertion of at least one IS-element.

In a last embodiment, the present invention also relates to the use of a *Lactobacillus delbrueckii* or a *Lactobacillus helveticus* for the preparation of a fermented product, wherein the *Lactobacillus delbrueckii* or the *Lactobacillus helveticus* is provided with a gene encoding, or affecting the production of, enzymes producing secondary metabolites, the β-galactosidase, the cell wall protease, the catabolite control protein A, the lactate dehydrogenase, a glycosyltransferase, a restriction system, a lysogenic prophage, or the permease of the lac operon, wherein said gene is inactivated by insertion of at least one IS-element.

DETAILED DESCRIPTION OF THE INVENTION

Within the following description, the percentages are given by weight except where otherwise stated, and the nucleotide sequences referred as "SEQ ID NO:" are always presented in the sequence listing hereafter.

Likewise, the expression "functional derivative" includes all nucleotide sequences which differ by substitution, deletion, addition of some nucleotides, for instance 1–50 nucleotides, but which keep their original activities or functions. A functional derivative may thus be due to the degeneracy of the genetic code. The selection of a functional derivative is considered to be obvious to one skilled in the art, since one may easily creates variants of an encoding sequence by slightly adapting methods known to one skilled in the art, for instance the methods described by Adams et al. (EP402450; Genencor), by Dunn et al (Protein Engineering, 2, 283–291, 1988), by Greener et al. (Strategies, 7, 32–34, 1994), and/or by Deng et al. (Anal. Biochem, 200, 81, 1992). In particular, a functional IS-element of the invention is considered as a derivative to another IS-element, if its sequence is at least 80% identical to the original IS-element, preferably at least 95%, for example. In the context of the present disclosure, the identity is determined by the ratio between the number of nucleotides of a derivative sequence which are identical to those of the original IS-element, and the total number of nucleotides of the said derivative sequence. Likewise, a functional IS-element of the invention may also be considered as a derivative to another IS-element if it can hybridize to it under very stringent conditions, that is to say that hybridizes always after a hybridization step at 65° C. during 15h in the buffer SSPE 1.5× (0.225 M NaCl, 0.0015 M EDTA, 0.015 M $NaH_2PO_4$ pH7) containing 1% SDS and 1% dehydrated milk, followed by 6 successive washing steps at 65° C. in different dilutions of SSC 10× (1.5 M NaCl, 0.15 M sodium citrate pH7, and 0.1% SDS), preferably respectively during 2 times 10 min with SSC 2×, during 2 times 10 min with SSC 1×, and during 2 times 5 min with SSC 0,1×.

With respect to first embodiment of the present invention, the use of an IS-element originating from lactobacillus species as a tool for genetically modifying the genome of *L. delbrueckii* or *L. helveticus*, is concerned. IS-elements can thus be used in genetic gene identification (tagging), gene inactivation, gene integration and/or gene expression on a plasmid and/or genomic level.

For identifying and/or inactivating genes from *L. delbrueckii* and *L. helveticus*, an IS-element may be placed on a bacterial plasmid, the plasmid may be introduced into the bacteria *L. delbrueckii* or *L. helveticus*, the transformed bacteria may then be subjected to conditions that inhibit replication of the plasmid so as to activate genomic integration of the whole plasmid (by way of the IS-element). Screening of genes that were thus inactivated may then be achieved by digesting the bacterial genome with restriction enzymes that do not cut into the integrated plasmid, ligating the digested products, introducing them into a bacteria in which the plasmid can replicate, selecting among the transformed bacteria digested products that contain the integrated plasmid, and identifying the gene in which the IS-element is inserted.

For integrating and/or expression genes into *L. delbrueckii* and *L. helveticus*, an IS-element may be placed on a bacterial plasmid comprising a gene of interest under control of regulatory sequences, this plasmid may be introduced into the bacteria *L. delbrueckii* or *L. helveticus*, the transformed bacteria may then be subjected to conditions that inhibit replication of the plasmid so as to activate genomic integration of the whole plasmid (by way of the IS-element), and the integrative bacteria may then further be subjected to conditions that activate expression of the gene of interest.

Preferably, IS-elements selected from DNA sequences SEQ ID NO:7–12, or functional derivatives thereof, are used for manipulating the genome of *L. delbrueckii* and *L. helveticus*.

With respect to second embodiment of the present invention, IS-elements originating from *L. delbrueckii* selected from the DNA sequences SEQ ID NO: 7–10 or functional derivatives thereof, are concerned. The DNA sequences SEQ ID NO:11 and 12 are not an object of the present invention because they were already described by Zwahlen et al. and Germond et al.

The third embodiment of the present invention concerns any *Lactobacillus delbrueckii* or *Lactobacillus helveticus* strain providing a gene encoding, or affecting the production of, enzymes producing secondary metabolites, the β-galactosidase, the cell wall protease, the catabolite control protein A, the lactate dehydrogenase, a glycosyltransferase, a restriction system, a lysogenic prophage, or the permease of the lac operon, wherein said gene is inactivated by insertion of at least one IS-element.

Enzymes producing secondary metabolites may be those that are involved in the production of compounds usually found in the typical yoghurt aroma, such as 1-nonen-3-one, 2,3-butanedione, 2,3-pentanedione, dimethyl sulfide, methional, 2-methyl-tetrahydrothiophen-3-one, 2E-nonenal, guaiacol, methyl propanal, 2-methyl butanal, 3-methyl butanal, 2- and 3-methyl-2-butenal, 2- and 3-methyl butyric acid, 3-methyl-2-butenethiol, 2-methyl furanethiol, 2-furfurylthiol, 3-mercapto-3-methylbutylformate, 4-ethyl guaiacol, 4-vinyl guaiacol, 2-isopropyl-3-methoxypyrazine, 2,3-diethyl-5-methylpyrazine, 2-ethyl-3,5-dimethylpyrazine, 2-isobutyl-3-methoxypyrazine, beta-damascenone, vanillin, 4-hydroxy-2,5-dimethyl-3(2H)-furanone, 2-ethyl-4-hydroxy-5-methyl-3(2H)-furanone, 3-hydroxy-4,5-dimethyl-2(5H)-furanone, and/or 5-ethyl-3-hydroxy-4-methyl-2(5H)-furanone (Lebensm. Wiss. u-Technol., 28, 78–86, 1995; EP97935535.1).

The β-galactosidase may be the LacZ of *L. delbrueckii*, or one of the two proteins LacL or LacM of *L. helveticus*. The cell wall protease may be one related to the protease described by Gilbert et al. (J. Bacteriol., 178, 3059–3065, 1996; see also EP810289). The catabolite control protein A may be one related to the CcpA described by Monedero et al. (J. Bacteriol., 179, 6657–6664, 1997). The lactate dehydrogenase may be one related to the lactate dehydrogenases described by Kochhar et al. (Eur. J. Biochem, 208, 799–805, 1992; Biochem. Biophys. Res. Commun., 185, 705–712, 1992). A glycosyltransferase may be one of the glycosyltransferases of *L. delbrueckii* or *L. helveticus*, respectively described in EP98201312.0 (Societe des Produits Nestle) and in EP98201311.2 (Société des Produits Nestlé).

Preferably, the *Lactobacillus delbrueckii* strain of the invention is a *Lactobacillus delbrueckii* sbp. *bulgaricus* or *Lactobacillus delbrueckii* sbp. *lactis*.

The *Lactobacillus delbrueckii* or *Lactobacillus helveticus* strain of the present invention may exist in nature, and thus may be selected by rapidly screening strains that are not capable of fermenting lactose and that contain at least an IS-element, for example an IS-element which is identical or derivating from the IS-elements providing the DNA sequences SEQ ID NO:7–12. Then, among the selected strains, one can easily identify those that contain an IS-element which is integrated into a gene of interest, i.e. a gene encoding the β-galactosidase.

In particular, screening of *Lactobacillus delbrueckii* or *Lactobacillus helveticus* strains that are not capable of fermenting lactose may be achieved on an X-gal plate to isolate colonies having a β-galactosidase mutation, i.e. mutants which are incapable of fermenting lactose due to a malfunction of the β-galactosidase enzyme (see also Mollet et al., J. of Bacteriology, 172, 5670–5676, 1990). These colonies of mutants may be subjected to a stability test by culturing them in a medium containing lactose as sole energy source, such cow's milk for example, in order to eliminate the mutants capable of returning spontaneously to the β-galactosidase normal state.

Likewise, screening of strains that contain at least one IS-element may be achieved by hybridizing the digested genomic DNA under stringent conditions with IS-element based probes, that are identical or derivating from the IS-element having the DNA sequences SEQ ID NO:7–12, for example. The genomic DNA may be extracted from the stable mutants by the method described by Delley et al. (Appl. Environ. Microbiol., 56, 1967–1970, 1990). The DNA may be digested with restriction enzymes such as, for example, Bam HI, Eco RI, HindIII, SalI and TaqI. The digested DNA may then be separated on agarose gel and placed on a transfer membrane for screening IS-element by (see the conditions described above). The IS-element based probes may be prepared by reverse-PCR from the genome of the lactic bacteria strains cited in the following example 1, by using primers prepared from each IS-element DNA sequence, for example.

Preferably, a *Lactobacillus delbrueckii* or *Lactobacillus helveticus* strain providing a β-galactosidase gene in which at least one IS-element is inserted may be obtained by genetic manipulation. To this end, an IS-element may be placed on a bacterial plasmid, the plasmid may be introduced into the bacteria *L. delbrueckii* or *L. helveticus*; the transformed bacteria may then be subjected to conditions that inhibit replication of the plasmid so as to activate genomic integration of the whole plasmid. Screening of strains containing an inactivated β-galactosidase gene may then be achieved by digesting the bacterial genome with restriction enzymes that do not cut into the integrated plasmid, ligating the digested products, introducing them into a bacteria in which the plasmid can replicate, selecting among the transformed bacteria digested products that contain the integrated plasmid, and selecting digested products that contain a β-galactosidase gene (lacM or lacL for *L. helveticus*).

*Lactobacillus delbrueckii* or *Lactobacillus helveticus* strains providing a β-galactosidase gene in which at least one IS-element is inserted are of potential interest for the industry. Accordingly, it is now possible to produce a yoghurt in which post-acidification and the appearance of a bitter taste during storage are significantly reduced, by using in combination a lactic bacteria that is capable of fermenting lactose and a *Lactobacillus delbrueckii* or a *L. helveticus* that contains at least one IS-element within the gene encoding the β-galactosidase. Accordingly, in a process of the present invention, a milk is fermented with a combination of at least one strain of a lactic bacteria that is capable of fermenting lactose, and a *Lactobacillus delbrueckii* or *Lactobacillus helveticus* providing a gene encoding the β-galactosidase that contains an IS-element.

Preferably, the *Lactobacillus delbrueckii* strain used in the present process is a *Lactobacillus delbrueckii* sbp. *bulgaricus* or *Lactobacillus delbrueckii* sbp. *lactis*.

The lactic bacteria that is capable of fermenting lactose may be any kind of lactic bacteria used in the dairy industry, for example bifidobacteria such as Bifidobacterium infantis and Bifidobacterium longum; lactococci such as *Lactococcus lactis* subsp. lactis, *Lactococcus lactis* subsp. cremoris and *Lactococcus lactis* subsp. lactic biovar diacetylactis, streptococci such as *Streptococcus thermophilus* and *Streptococcus faecalis*; lactobacilli such as *Lactobacillus delbrueckii* subsp. *bulgaricus*, *Lactobacillus acidophilus* (comprising 6 sub-groups such as *L. johnsonii*; see Fujisawa et al., Int. J. Syst. Bact., 42, 487–491, 1992), *Lactobacillus helveticus, Lactobacillus farciminis, Lactobacillus alimentarius, Lactobacillus casei* subsp. *casei, Lactobacillus delbruckii* subsp. *lactis, Lactobacillus sake* and *Lactobacillus curvatus*.

The starting material used to carry out the process according to the invention for the production of a yogurt may be an animal and/or vegetable, fresh or reconstituted, skimmed, semi-skimmed or whole, pasteurized milk having a dry matter content of 10 to 20% by weight. This milk is preferably inoculated with 0.2 to 5% and, more preferably, with 0.5 to 3% by volume a culture containing $10^6$–$10^{10}$ and preferably $10^8$–$10^9$ cells/ml of the *Lactobacillus delbruekii* or *Lactobacillus helveticus* mutant, and 1–5% and preferably 2–4% by volume of a culture containing $10^6$–$10^{10}$ and preferably $10^8$–$10^9$ cells/ml of a lactic bacteria capable of fermenting lactose, preferably a *Streptococcus thermophilus*.

The milk may be fermented for 2.5 to 15 h at 35 to 48° C. The pH value reached during fermentation or acidification may vary between about 4.3 and 5. This pH may also be reduced by approximately 0.05 to 0.3 unit by addition of approximately 0.2 to 2% by weight glucose to the starting milk.

Accordingly, the yogurt shows organoleptic qualities having the typical character of traditional yogurt due to the use in symbiosis of mutants of *L. delbrueckii* or *L. helveticus* with lactic bacteria capable of fermenting lactose, preferably any *S. thermophilus*. It may be kept for several weeks under refrigeration or even at ambient temperature for the second embodiment without the pH value falling by more than about 0.05–0.5 unit, without the appearance of a bitter taste and without the number of living cells which it contains showing significant variations.

The present invention is not to be limited in scope by the specific embodiments described herein. Indeed, various modifications of the invention, in addition to those described herein, will become apparent to those skilled in the art from the foregoing description. Such modifications are intended to fall within the scope of the claims. Various publications are cited herein, the disclosures of which are incorporated by reference in their entireties to the extent necessary for understanding the present invention. DNA manipulation, cloning and transformation of bacteria cells are, except where otherwise stated, carried out according to the textbook of Sambrook et al. (Sambrook et al., Molecular Cloning, A Laboratory Manual, Cold Spring Harbor Laboratory Press, U.S.A., 1989).

The strains *Lactobacillus delbrueckii* sbp. *bulgaricus* CNCM I-800 and CNCM I-2009, and *Lactobacillus delbrueckii* sbp. lactis CNCM I-2008 were deposited under the Budapest Treaty, at the Collection Nationale de Culture de Microorganismes (CNCM), 25 rue du docteur Roux, 75724 Paris. France, respectively on Oct. $4^{th}$, 1988 (CNCM I-800). and May $7^{th}$, 1998 (CNCM I-2008 and I-2009). All restrictions as to the availability of these deposits will be withdrawn upon first publication of this application or another application which claims benefit of priority to this application.

The strains *Lactobacillus helveticus* ATCC15807 and ATCC11977, and *Lactobacillus delbrueckii* sbp. *bulgaricus* ATCC11842 and NCDOB19 can be obtained respectively at the American Type Culture Collection (ATCC), 12301 Parklawn Drive, Rockville, Md. 20852, US, and at the National Collection of Food Bacteria (for the NCDO

Example 1

Identification of *L. delbrueckii* IS-elements

Media and Chemicals: all lactobacilli were grown in Difco lactobacillus MRS broth (De Man, 1960). *E. coli* was grown in YT broth 2× prepared according to Sambrook et al. (1989). For plasmid selection and maintenance in *E. coli*, ampicillin (100 ug/ml) was added to the growth medium.

Bacteria and Plasmids: the strains were stored 10 times concentrated in MRS broth containing 10% glycerol at −80° C. The same storage procedure was used for *E. coli* strains in their respective media (see above). Cloning procedures were carried out by using pUC19 (Yanisch-Perron et al., Gene, 33, 103–119, 1985) and *E. coli* strain BZ234 (Biocentrum, University of Basel, Switzerland).

Chromosomal DNA Preparation: lactobacilli genomic DNA was prepared as described by Delley et al. (Appl. Env. Microb., 56, 1967–1970, 1990).

DNA Sequencing: DNA sequences were determined by the dideoxychain termination method using T7 DNA polymerase sequencing kit (Pharmacia, LKB) or directly by PCR using the finol DNA sequencing KIT (Promega) (Sanger et al., 1977). This last kit was finally exclusively used even to sequence plasmid DNA fragments.

ISL4 was obtained by PCR on the genomic DNA of CNCM I-2008 strain with the oligos SEQ ID NO:1 and 2. The amplified fragment was cloned into the SmaI site of pUC19 and further subcloned for sequencing. To verify the sequence, the same was done with other *L. delbrueckki* strains.

ISL5 was sequenced from ATCC11977 strain directly from an amplified PCR fragment obtained with oligos SEQ ID NO:5 and 6. The complete nucleotide sequence was then realised by PCR sequencing with internal oligos. To verify the sequence, the same was done with other *L. delbrueckii* strains.

ISL6 and ISL7 were sequenced directly by PCR from strains NCDOB19 and CNCM I-2009, respectively, using oligos SEQ ID NO:3 and 4.

DNA Manipulations: agarose gel electrophoresis, restriction enzyme digestions, ligations and transformations in *E. coli* were performed according to standard procedure (Sambrook et al., 1989). Plasmid DNA from *E. coli* was purified by the alkali lysis method (Sambrook et al., 1989).

DNA amplification was done by polymerase chain reaction (PRC) in the presence of 0.2 mM of each dNTPs, 1 μM of each oligonucleotide primers, the appropriate buffer and the Taq polymerase (SuperTaq, Endotell, Allschwill, CH; BioTaq, Bioprobe system, Montreuil sous Bois, France).

Chromosome walking was performed by the inverted PCR method. Chromosomal DNA was digested to completion with a chosen restriction enzyme close to the end of the known sequence and self-ligated at a concentration of 1 μg/ml under standard conditions. The ligated DNA was concentrated at 10 μg/ml by centrifugation through a Ultrafree-MC filter with a cut off of 30,000 (Millipore, Bedfore, USA) and used for PCR reaction using oligonucleotides in opposite orientation and localised between the restriction enzyme cut and the end of the known sequence (Triflia et al., Nucleic Acids Res., 16, pp8186, 1988). If necessary, the amplified DNA was blunt ended with $T_4$ DNA polymerase (Sambrook et al., 1989), cloned into the SmaI site of pUC19 or cloned directly in pGEMT (Promega).

Identification of ISL4: ISL4 was identified in strain CNCM I-2008, when EcoRI digested DNA of this strain highlighted a fragment of 4.5 kb instead of 3.3 kb in ATCC11842 and CNCM I-800 with ISL3 as probe (see Germond et al., 1995). The 2.3 kb fragment resulting from a PCR amplification in CNCM I-2008 was cloned and sequenced. The sequence revealed a gene, coding for a transposase homologous (19.1% identity) to the transposase of the IS116 of *Streptomyces clavuligerus* (Leskiw et al., J. Gen. Microbiol., 136, 1251–1258, 1990). This IS-element is 1655 bp long and, like IS116, induces no target site duplication and has no inverted repeated sequences at its ends. The DNA sequence of ISL4 is given in the following list of DNA sequences under the reference SEQ ID NO:7.

Identification of ISL5: identified upstream lacS, the IS-element ISL5 containing an integrated copy of ISL4 was sequenced in strains ATCC11842 and CNCM I-800. Only short open reading frames could be detected. A copy of ISL5, with no ISL4 integrated, was isolated from the *L. helveticus* strain ATCC11977. ISL5 is 1,589 bp long and contains 2 overlapping ORFs of 224 and 270 amino acids whose sequence showed no homology with any known IS-element. The genes are flanked by an imperfect inverted repeat of 65 bp and a 7 bp target site duplication. The DNA sequence of ISL5 is given in the following list of DNA sequences under the reference SEQ ID NO:8.

Identification of ISL6: ISL6 was found in *L. delbrueckii* strains during the study of the intergenic region between the thiogalactose acetyltransferase (lacA) gene and the lacS gene. A PCR amplification of this region let appear DNA fragments of variable lengths according to the strains. This region sequenced in strain NCDOB19 revealed a gene coding for a transposase homologous (45% identity) to the transposase of IS150 of *E. coli* K12 (Schwartz et al., Nucleic Ac. Res., 16, 6789–6802, 1988). A leucine (TTG) with a ribosome binding site (RBS) at the correct distance was chosen as a potential start of the gene. This gene was part of an IS-element of 1,457 bp long with imperfect inverted repeats of 24 bp and a bp target site duplication. ISL6 is located in the terminator region of lacA and provides the DNA sequence SEQ ID NO:9.

Identification of ISL7: ISL7 was found in the lac operon of *L. delbrueckii*. It is located in the lac operator of strain CNCM I-2009, close to ISL6. This region was sequenced in this strain and revealed a gene coding for a transposase homologous (29.4% identity) to the transposase of the IS30 of *E. coli* K12 (Caspers et al. Mol. Gen. Genet., 196, 68–73, 1984). The transposase gene is flanked by imperfect inverted repeats of 28 bp and a long sequence of 13 bp was used as target site and duplicated. This element was the smallest IS-element found in *L. delbrueckii* with only 1,238 bp. The DNA sequence of ISL7 is given in the following list of DNA sequences under the reference SEQ ID NO:10.

Example 2

Insertion of an IS-element from *L. delbrueckii* into the β-Galactosidase Gene of *L.delbruekii* or *L. helveticus*

*L. delbrueckii* strains NCDOB19 and CNCM I-2009 were each grown over-night at 42° C. in 10 ml MRS broth (De Mam et al., 1960) and the cells were harvested by centrifugation (5 min. at 2,000×9). Genomic DNA was then prepared from those cells as described by Delley et al., 1990. Purified DNA was stored each 250 μl in TE (20 mM Tris-HCl pH 7.5, 1 mM EDTA) at 4° C. DNA fragments containing ISL6 (from NCDOB19 strain) and ISL7 (from CNCM I-2009 strain) were amplified by making use of the polymerase chain reaction (PCR). For that, 10–50 ng of genomic DNA was mixed with 0.2 mM of each dNTPs, 1 µM of oligonucletoide primers (i.e. primers SEQ ID NO:13 and NO:14 for ISL6, and primers SEQ ID NO:15 and NO:16 for ISL7) in a total volume of 25 µl of the appropriate buffet. Amplification was done in the presence of 1 unit of DNA Tag polymerase (super Tag, Endotell AG, Allschwill, Switzerland) according to the supplier's instructions, by 30 cycles of 1 min. at 95° C., 1 min at 45° C. and 2 min at 72° C. on a Perkin-Elmer thermocycler (DNA thermal cycler, Perking Elmer, N.J., U.S.A.).

4 µl of the PCR mix were transferred to a new Eppendorf tube and digested with the restriction enzymes SalI and PstI (Boehringer Mannheim, Germany; New England Biolabs, U.S.) in a total volume of 75 µl for 2 hrs and 37° C. according to the instruction of the suppliers. The restricted DNA was first extracted once by phenol and then precipitated by ethanol (Sambrook et al., 1989). Dried DNA was resuspended in 10 µl TE and kept on ice.

In parallel, 2 µl of purified plasmid DNA pG+host9 (Maguin et al., J. Bact., 178, 931–935, 1996) was suspended in 150 µl of TE and restricted with SalI and PstI for 2 hrs at 37° C. according to the instruction of the suppliers. After digestion, the DNA was loaded onto a 0.8% agarose gel and migrated at 80 V at room temperature. After staining with ethnidium bromide and visualisation under UV, a ca. 3.7 kb fragment was visible. This fragment was cut out of the gel, and the DNA extracted by using filtration through a 0.45 µ ultrafree MC filter unit, followed by a phenol extraction, ethanol precipitation and resuspension in TE. The PCR amplified ISL6 and ISL7 were ligated into pG+host9 plasmid by ligating each 200 ng of PCR fragment with 100 ng of PG+host9 DNA in a total volume reaction of 10 µl, supplemented with appropriate buffer and 1 Unit of T4 DNA ligase (Boehringer and New England Biolabs) according to the instruction of the suppliers, at 12° C. for 4 hrs. The ligation mixes were then transformed by electroporation to competent *E. coli* XL-1 Blue (Stratagene, La Salla, U.S.) according to the method described by Sambrock et al., 1989. Selection for transformants was on LB plates (0.5% NaCl, 1% trypotone, 1% yeast extract) supplemented with 2 mg/ml erythromycin at 37° C. overnight. Single colonies were picked into 15 ml LB erythromycin, and grown at 37° C. 10 ml of the cultures were used to extract the plasmid by using the alcalin method (Q1Aprep8 miniprep K.7 from Quiagen). The plasmids were then checked for the presence of the cloned ISL6 and ISL7 by restriction analysis and agarose gel electrophoresis. Correct clones were named pG+host9-ISL6 and pG+host9-ISL7 respectively. Larger scale DNA preparations of the two plasmids were prepared by JETstar maxi kit from Genomed.

The two plasmids were independently transferred to strains of the *L. delbrueckii* sbp. *bulgaricus* (the ATCC11842 strain) and *L. helveticus* species according to the methods reported by Sasaki et al (FEMS Microbiology Reviews, 12, Fourth Symposium on Lactic Acid Bacteria, Noordwijkerhout, The Netherlands, 1993; Satoh et al., Appl. Env. Microb., 63, 4593–4596, 1997), and Bhowmik et al. (J. Bacteriol, 175, 6341–6344,1993).

After the genetic transfer, lactobacilli were plated onto MRS plates containing 25 µl/ml X-gal (5-bromo-4-chloro-3-indolyl-µ-D-galacto-pyranoside) and incubated in microaerophilic conditions as described in Mollet and Delley (J. Bact., 172, 5670–5676, 1990). With a rare frequency, white colonies were identified among mostly blue colonies on these agar plates, and they were picked, purified and stored ten times concentrated in MRS containing 10% glycerol at −80° C.

In order to identify ISL6 and/or ISL7 integrated into the lacZ gene of *L. delbrueckii* sbp. *builgaricus*, or lacL or lacM genes of *L. helveticus*, genomic DNA of the lactobacilli was prepared according to Delley et al., and used in Southern hybridisation experiments by using a radioactive labelled PCR fragment carrying the β-glactosidase gene (oligos SEQ ID NO:17 and NO:18 for *L. delbrueckii* sbp. *bulgaricus*; oligos SEQ ID NO:19 and NO:20 for *L. helveticus*).

Example 3

Insertion of an IS-element Into the Cell Wall Protease Gene of *L.delbruekii* and *L. helveticus*

In this example, the same genetic constructions were used as in Example 2. The two plasmids were transferred to *L. delbrueckii* and *L. helveticus* as described in Example 2. After the genetic transfer, the lactobacilli were plated onto MSK agar plates (10% reconstituted skimmed milk, 1.5% agar) and allowed to grow under anaerobic conditions at 420° C. Among regular, large bacterial colonies, very few small colonies can be observed. Such small colonies were isolated, single cell purified and stored at ten times concentration in MRS with 10% glycerol at −80° C.

As described in Example 2, genomic DNA of the lactobacilli was prepared and analysed by Southern blot hybridisation. In a few cases, ISL6 and ISL7 insertions into the prtB gene encoding the cell-wall bound protease, could be observed. As radioactive labelled probe, the prtB gene as described by Gilbert et al. (J. Bacteriol., 178, 3059–3065, 1996) was used.

Example 4

Expression of a Gene of Interest by use of IS-elements

In this example, the same genetic constructions were used as in Example 2. The two plasmids were transferred to *L. delsbrueckii* and *L. helveticus* as described in Example 2. After the genetic transfer, the lactobacilli were plated onto MRS agar plates supplemented with 5 µg/ml erythromycin, and allowed to grow under anaerobic conditions at 42° C. After several days of incubation, colonies of erytiromycin resistant lactobacilli were identified and stored at −80° C., as described in Example 2. Genomic DNA of the lactobacilli was prepared and analysed by Southern blot analysis, as described in Example 2. As radioactive labelled DNA probes, plasmid pG+host9 DNA was used.

The results indicated, that in a few cases, plasmid pG+host9 was integrated into the bacterial genome, flanked by the respective IS-element in direct orientation. Hence, the erythromycin resistance gene was functionally integrated onto the genome by making use of the integrative activity of the IS-elements.

Example 5

Insertion of an IS-element from *L. helveticus* in the β-galactosidase Gene of *L. helveticus* and *L. delbrueckii* sbp. *bulgaricus*

*L. helveticus* strain ATCC15807 was grown in 10 ml MRS broth overnight at 42° C., and cells were harvested by centrifugation. Genomic DNA was then prepared as described by Delley et al. A DNA fragment containing ISL2 was amplified by PCR, using primers SEQ ID NO:21 and NO:22, in the same way as explained in Example 2. The DNA fragment was digested with SalI and PstI, as described above. In parallel, plasmid DNA pG+host9 was digested with SalI and PstI, and purified by agarose gel electrophoresis as described above. The amplified DNA fragment containing ISL2 was then cloned into pG+host9, transformed to *E. coli* XL-1 blue, and erythromycin resistant colonies were isolated on LB plates supplemented with 2 mg/ml erythromycin at 37° C. Plasmid DNA was extracted and analysed by restriction analysis. Correct clones were named pG+host9-ISL2.

Plasmid pG+host9-ISL2 was transferred to *L. helveticus* ATCC15807 according to Bhowmik et al., and to *L. delbrueckii* sbp. *bulgaricus* (the ATCC11842 strain) according to Satoh et al.

Transformants were selected on MRS agar plates supplemented with 4 μg/ml erythromycin at 35° C. incubation. Individual colonies were grown up in MRS without erythromycin and by shifting the temperature of incubation from 35° C. to 42° C. Cultures were then diluted in fresh MRS and plated onto MRS X-gal plates, containing 25 μg/ml 5-bromo-4 chloro-3-indolyl-β-D-galactopyranoside, and incubated in micro-aerophilic conditions at 42° C. After 1–2 days, with a rare frequency, white colonies were identified among mostly blue colonies. They were isolated, cultured at 42° C. in MRS broth, and their genomic DNA isolated as described above. Southern blot analysis with using as probe a radioactive labelled PCR fragment (oligos SEQ ID NO:17 and NO:18 for *L. delbrueckii* sbp. *bulgaricus*; oligos SEQ ID NO:19 and NO:20 for *L. helveticus*) allowed to identify clones having ISL2 integrated in the β-galactosidase genes (lacL or lacM for *L. helveticus*). Such clones were lactose negative, i.e. unable to grow on lactose as unique carbon source as e.g. present in milk.

Example 6

Yogurt Preparation 0.2 litres MRS culture medium are sterilized for 15 minutes at 121° C., and then inoculated with 5% by volume of an active culture of the ATCC11842 *L. delbrueckii* sbp. *bulgaricus* strain from example 2 carrying ISL6 integrated into the β-galactosidase producing lacZ gene. This active culture contains approximately $10^9$ cells/ml. After incubation for 8 h at 41° C., a starter containing $4.5 \times 10^8$ cells/ml is obtained.

5 litres reconstituted skimmed milk having a dry matter content of 10%, to which 0.1% yeast extract has been added, are sterilized for 15 minutes at 121° C., and inoculated with 2% of an active culture of commercial thickening *Streptococcus thermophilus* containing approximately 109 cells/ml. After incubation for 4 h at 41° C., a starter containing $4.5 \times 10^8$ cells/ml is obtained.

One batch of whole milk containing 3.7% fats strengthened with 2.5% skimmed milk powder and pasteurized for 30 min at 90° C. is then inoculated with 2% by volume of the starter of "*L. bulgaricus*" and 3% by volume of the starter *S. thermophilus*. The inoculated milk is stirred, poured into pots and incubated for 4 h at 41° C. The yogurt obtained has a good firm and smooth texture and an agreeable mild flavour typical of this type of product. It has a pH of 4.53 and contains $4.8 \times 10^7$ cells/ml of "*L. bulgaricus*" and $7 \times 10^8$ cells/ml of *S. thermophilus*.

This yogurt is subjected to a storage test at 4° C. and 12° C. In this test the pH is measured and the product is tasted after storage for 1, 7, 14 and 24 days. By way of comparison, yogurt preparations and storage analysis are repeated by replacing the "*L. bulgaricus*" mutant by its mother strain ATCC11842 which can be used industrially for the production of yogurts.

For yogurts containing the "*L. bulgaricus*" mutant, the pH decreases to a minimum of 4.40 after 24 days at 4° C., and to a minimum of 4.15 after 24 days at 12° C. For yogurts containing the mother strain ATCC11842, the pH decreases to a minimum of 4.10 after 24 days at 4° C., and to a minimum of 3.90 after 24 days at 12° C. This show that the yogurts containing the "*L. bulgaricus*" mutant are highly stable in storage, their post-acidification being far less rapid than of the comparison yogurt. Finally, in contrast to the comparison yogurt, no appearance of even slight bitter taste is observed.

Example 7

Acidified Milk

A *L. helveticus* mutant from example 5 which has integrated ISL2 within a β-galactosidase gene, is used in combination with a commercial *S. thermophilus* for preparing an acidified milk. The conditions used are those presented in example 6, with the difference that the *L. bulgaricus* mutant is replaced by the *L. helveticus* mutant.

What is claimed is:

1. A method of using an insertion sequence element as a tool for genetically modifying the genome of *Lactobacillus delbrueckii* or *Lactobacillus helveticus* comprising:

inserting the insertion sequence element into a bacterial plasmid, wherein the insertion sequence element is selected from DNA sequences of SEQ ID NO: 7, 8, 9, or 10 or a functional derivative thereof, wherein the derivative hybridizes to a complement of SEQ ID: 7, 8, 9, or 10, under very stringent conditions;

introducing the plasmid into *Lactobacillus delbrueckii* or *Lactobacillus helveticus*;

subjecting the *Lactobacillus delbrueckii* or *Lactobacillus helveticus* to conditions that inhibit replication of the plasmid; and screening for genes that were inactivated or subjecting the *Lactobacillus delbrueckii* or *Lactobacillus helveticus* to conditions that activate expression of a gene of interest.

2. The method according to claim 1, wherein the insertion sequence elements are used for screening experiments to identify a function of a polypeptide encoded by a gene, for integration experiments or for gene expression in the bacterial genome of *Lactobacillus delbrueckii* or *Lactobacillus helveticus*.

3. The method according to claim 1, wherein insertion sequence elements are used to genetically modify the genome of *Lactobacillus delbrueckki* subspecies bulgaricus or *Lactobacillus helveticus* subspecies lactis.

4. The method according to claim 1, wherein a gene in *Lactobacillus delbrueckii* or *Lactobacillus helveticus* is inactivated by at least one insertion sequence element.

5. The method according to claim 1, wherein a gene in *Lactobacills delbrueckii* or *Lactobacillus helveticus* is activated by at least one insertion sequence element.

6. The method according to claim 4, wherein the gene that is inactivated is a β-galactosidase gene.

7. The method according to claim 1, wherein the genetically modified *Lactobacillus delbrueckii* or *Lactobacillus helveticus* provides a gene encoding or affecting the production of enzymes producing secondary metabolites, β-galactosidase, cell wall protease, catabolite control protein A, lactate dehydrogenase, glycosyltransferase, a restriction system, a lysogenic prophage, or permease of a lac operon, wherein said gene is inactivated by insertion of at least one insertion sequence element.

8. The method of claim 1, wherein the genetically modified *Lactobacillus delbrueckii* or the *Lactobacillus helveticus* is used in the preparation of a fermented product, wherein the *Lactobacillus delbrueckii* or *Lactobacillus helveticus* is provided with a gene encoding or affecting the production of enzymes producing secondary metabolites, β-galactosidase, cell wall protease, catabolite control protein A, lactate dehydrogenase, glycosyltransferase, a restriction system, a lysogenic prophage, or permease of a lac operon, wherein said gene is inactivated by insertion of at least on insertion sequence element.

* * * * *

UNITED STATES PATENT AND TRADEMARK OFFICE
CERTIFICATE OF CORRECTION

PATENT NO. : 6,331,140 B1
DATED : December 18, 2001
INVENTOR(S) : Mollet et al.

It is certified that error appears in the above-identified patent and that said Letters Patent is hereby corrected as shown below:

Title page,
Replace the "ABSTRACT" with the following:
-- A method of using an IS-element, originating from *Lactobacillus delbrueckii* selected from DNA sequences of SEQ ID NO: 7 - 10, or functional derivatives thereof, as a tool for genetically modifying the genome of *Lactobacillus delbrueckii* or *Lactobacillus helveticus*, wherein the *Lactobacillus delbrueckii* or *Lactobacillus helveticus* provides a gene encoding or affecting the production of enzymes producing secondary metabolites, B-galactosidase, cell wall protease, catabolite control protein A, lactate dehydrogenase, glycosyltransferase, a restriction system, a lysogenic prophage, or permease of a lac operon and the gene is inactivated by insertion of at least one insertion sequence element. Additionally, use of the above-mentioned *Lactobacillus delbrueckii* or *Lactobacillus helveticus* for the preparation of a fermented product. --

Column 25,
Lines 59-60, replace "bulgarcu-sor" with -- bulgarcus or --.

Column 26,
Line 36, replace "*Lactobacills*" with -- *Lactobacillus* --; and
Line 58, replace "on" with -- one --.

Signed and Sealed this

Sixteenth Day of April, 2002

*Attest:*

JAMES E. ROGAN
*Attesting Officer*     *Director of the United States Patent and Trademark Office*